(12) United States Patent
Staniforth et al.

(10) Patent No.: US 6,990,974 B2
(45) Date of Patent: Jan. 31, 2006

(54) MOUTHPIECE FOR A PARTICULATE INHALER

(75) Inventors: John Nicholas Staniforth, Bath (GB); David Alexander Vodden Morton, Bath (GB); Iain Grierson McDerment, Herts (GB)

(73) Assignee: Andi-Ventis Limited, (CY)

( * ) Notice: Subject to any disclaimer, the term of this patent is extended or adjusted under 35 U.S.C. 154(b) by 42 days.

(21) Appl. No.: 10/226,295

(22) Filed: Aug. 22, 2002

(65) Prior Publication Data

US 2004/0035412 A1 Feb. 26, 2004

(51) Int. Cl.
*A61M 11/00* (2006.01)
*A61M 13/00* (2006.01)

(52) U.S. Cl. ............... 128/200.18; 128/200.23; 604/58

(58) Field of Classification Search ........... 128/200.11, 128/200.12, 200.14, 200.15, 200.17, 200.18, 128/200.23, 203.12, 203.13, 203.15, 203.18, 128/203.19, 203.21, 201.26, 202.21; 604/57–64
See application file for complete search history.

(56) References Cited

U.S. PATENT DOCUMENTS

| 4,739,754 | A | * | 4/1988 | Shaner | 128/203.15 |
| 4,907,583 | A | * | 3/1990 | Wetterlin et al. | 128/203.15 |
| 5,033,463 | A | * | 7/1991 | Cocozza | 128/203.21 |
| 5,207,217 | A | * | 5/1993 | Cocozza et al. | 128/203.21 |
| 5,582,162 | A | * | 12/1996 | Petersson | 128/203.15 |
| 5,676,130 | A | * | 10/1997 | Gupte et al. | 128/203.19 |
| 5,724,959 | A | * | 3/1998 | McAughey et al. | 128/203.15 |
| 5,894,995 | A | * | 4/1999 | Mazzei | 239/489 |
| 6,026,808 | A | * | 2/2000 | Armer et al. | 128/200.23 |
| 6,065,472 | A | * | 5/2000 | Anderson et al. | 128/203.21 |
| 6,230,704 | B1 | * | 5/2001 | Durkin et al. | 128/200.22 |
| 6,257,232 | B1 | * | 7/2001 | Andersson et al. | 128/203.15 |

FOREIGN PATENT DOCUMENTS

WO   WO 97/25086   *   7/1997   ............ 128/203.23

* cited by examiner

*Primary Examiner*—Teena Mitchell
(74) *Attorney, Agent, or Firm*—George R. McGuire; Bond, Schoeneck & King, PLLC

(57) ABSTRACT

A mouthpiece for use in an inhaler for a particulate medicament, the mouthpiece having: an inlet and an outlet for the particulate medicament; a number of abutments which extend across the mouthpiece and which are arranged in a staggered configuration such that, in use, medicament is caused to break up as the medicament passes through the mouthpiece; wherein the abutments are blades having an elongate cross section in the direction of travel of the medicament.

15 Claims, 2 Drawing Sheets

MOUTHPIECE FOR A PARTICULATE INHALER

BACKGROUND OF THE INVENTION

This invention relates to particulate inhalers and, in particular, to a mouthpiece for such an inhaler, the mouthpiece being provided with means for ensuring that the particle size of the entrained medicament is minimised.

Mouthpieces for inhalers in the prior art have used many different means for breaking up the particulate medicament which is being inhaled by the patient. Such means include the use of staggered teeth, screens, baffle plates, and filters.

In particular, as disclosed in EP 0237507, it is known to provide one or more deflector devices which are arranged in a stationary configuration within a mouthpiece of the inhaler such that the air flow is accelerated in the region of the deflector devices due to a constriction of the cross section of the mouthpiece. The air flow is caused to accelerate centripetally such that particles or aggregates of the compound are ground into smaller particles by colliding with each other and/or by impacting on the walls of the deflector devices.

A major disadvantage with such an arrangement is that, because the flow area through the mouthpiece is constricted, there is an increase in the inhalation resistance which means that it is more difficult for patients having respiratory diseases to obtain the correct dosage of the medicament.

WO 97/25086 discloses a powder inhalation device which includes a series of baffles past which the air flow with entrained medicament is caused to flow. The flow passes along one surface of each baffle until it contacts a further baffle, causing the air flow to change flow direction within a delivery conduit. Such changes in flow direction reduce the flow rate of the medicament and increases the inhalation resistance.

SUMMARY OF THE PRESENT INVENTION

Accordingly, the present invention is directed to providing a mouthpiece for use in an inhaler for particulate medicament to break up agglomerations of drug particles but without creating an increased inhalation resistance during use.

According to the present invention, there is provided a mouthpiece for use in an inhaler for a particulate medicament, the mouthpiece having:

an inlet and an outlet for the particulate medicament;

a number of abutments which extend across the mouthpiece and which are arranged in a staggered configuration such that, in use, medicament agglomerations are caused to break up as the medicament passes through the mouthpiece;

characterised in that the abutments are blades having an elongate cross section in the direction of travel of the medicament from the inlet to the outlet and around which, in use, medicament is caused to pass.

Medicament may collide with a surface of at least one of the abutments to encourage deagglomeration. Alternatively, a portion of the medicament may be deflected such that it collides with either a wall of the mouthpiece or with other agglomerates of medicament. Further, the deagglomeration may be caused by a shearing action of the air as it passes over agglomerations of medicament.

Preferably, the blades are provided with leading and/or trailing edges which are sharp. This ensures that little or no deposition of medicament is generated on either of the edges. A circular cross section of the blades was tested, but it was noted that static zones were created in the air flow around the abutments, leading to significant deposition of medicament on the leading and trailing edges. A further disadvantage of the circular cross-section is that the abutments are not sufficiently aerodynamically shaped so as not to affect the inhalation resistance. Accordingly, the elongate arrangement of the blades of the present invention provides the optimum solution.

Preferably, the blades are arranged such that the longer axes of their cross-section are parallel to the air flow through the mouthpiece.

The blades may be arranged in columns, from the inlet to the outlet.

Preferably, the longer axes of the cross-sections of adjacent blades in the same column are separated, in a direction perpendicular to the planes in which the blades lie, by between 1.5 mm and 2.5 mm, and more preferably by between 1.8 mm and 2.2 mm. The longer dimension of the cross-section of the blades may be between 3.8 mm and 4.8 mm, preferably between 4.1 mm and 4.5 mm.

The shorter axes of the cross-sections of blades in adjacent columns may be separated, in the direction of the air flow, by between 4 mm and 5 mm, preferably by 4.5 mm. The shorter dimension of the cross-section of the blades may be between 0.6 mm and 1.2 mm, preferably 0.9 mm.

Preferably, particle deflectors project from the inner surface of the wall of the mouthpiece such that they act as extra blades. The provision of these additional particle deflectors ensures that there is no straight line path in the direction of the air flow through the mouthpiece for the particulate medicament such that the flow of the medicament must always be disrupted.

BRIEF DESCRIPTION OF THE DRAWINGS

One embodiment of the present invention will now be described with reference to the accompanying drawings in which.

DETAILED DESCRIPTION OF A PREFERRED EMBODIMENT

Figure 1:
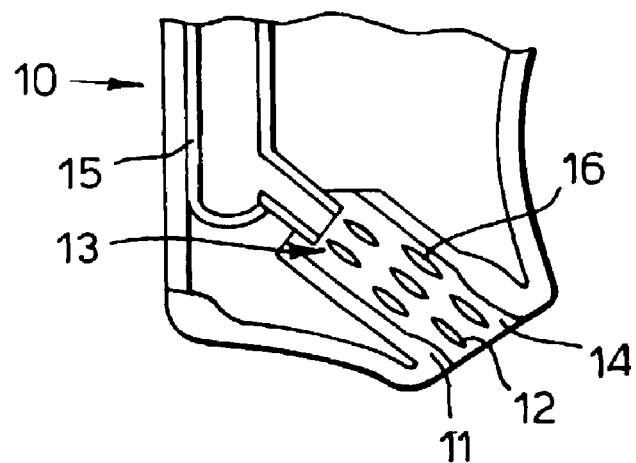
FIG. 1 is a cross sectional view through part of an inhaler having a mouthpiece according to the present invention.
Figure 2:
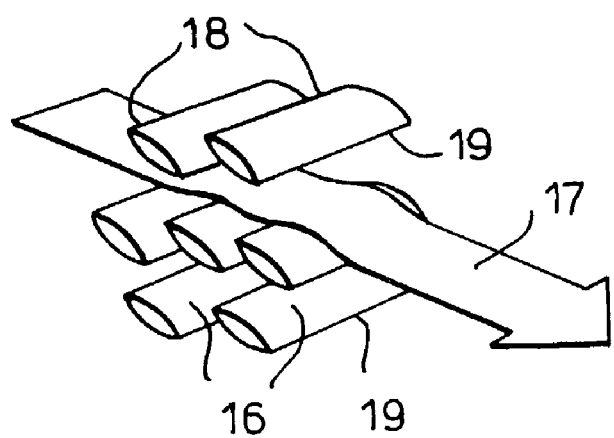
FIG. 2 is a perspective view of the arrangement of the blades in the present invention.

As can be seen from FIG. 1 and FIG. 2, an inhaler 10 is provided with a mouthpiece 11 having a passageway 12 through which particulate medicament (not shown), entrained in an air stream, is drawn in use. The passageway 12 has an inlet 13 and an outlet 14. The inlet 13 of the mouthpiece is in fluid communication with a supply tube 15 through which the particulate medicament is drawn, entrained in an air flow. A number of blades 16 are provided extending across the passageway 12. The blades 16 are arranged in a staggered configuration such that the air flow, indicated by arrow 17 in FIG. 2, is forced to take a tortuous path from the inlet 13 to the outlet 14 of the mouthpiece 11. The blades 16 are elongate in cross-section in the direction of air flow and have leading 18 and trailing 19 edges which are sharp.

Figure 3:
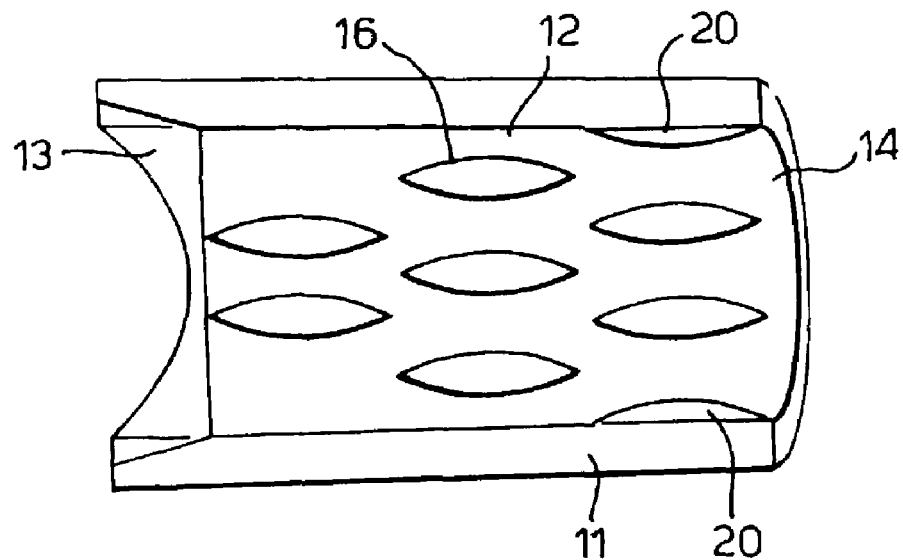
FIG. 3 is a cross sectional view of a mouthpiece according to the present invention.

In FIG. 3, the arrangement of the blades 16 can clearly be seen. Additional particle deflectors 20 are provided near the nominally upper and lower regions of the mouthpiece 11.

These deflectors 20 may take the form of a half blade such that they have the same outer curved surface.

Figure 4:
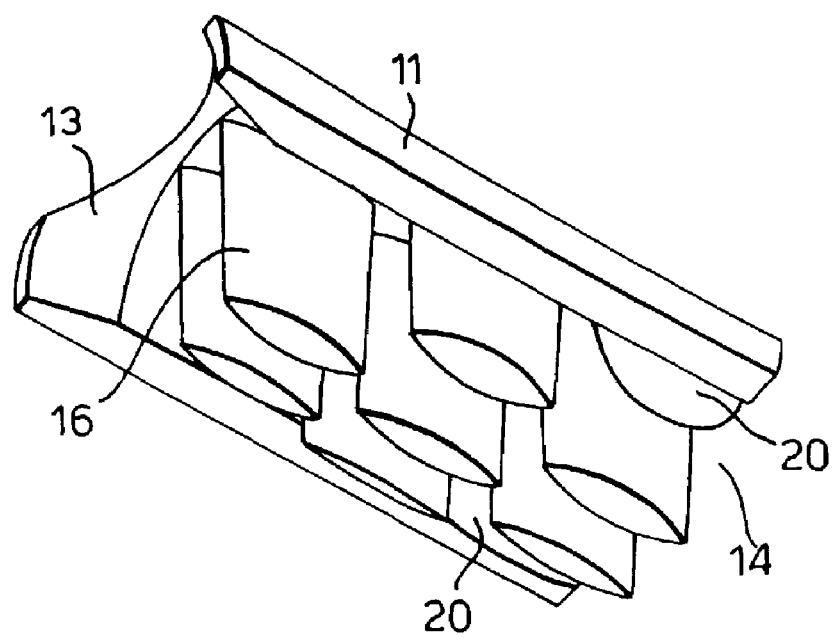
FIG. 4 is a perspective view of one half of a mouthpiece.

FIG. 4 shows a perspective view of one half of the mouthpiece 11. As can be clearly seen, the blades 16 and the particle deflectors 20 are formed so as to abut with the corresponding inner surface of the other half of the mouthpiece 11. Such an arrangement ensures that no particles entering the inlet 13 can travel to the outlet 14 without having their flow disrupted by at least one surface of either the blade 16 or the particle deflector 20.

What is claimed is:

1. A mouthpiece for use in an inhaler for a particulate medicament, said mouthpiece comprising:
    a passageway extending along a longitudinal axis and having an inlet and an outlet for said particulate medicament to be drawn through; and
    a plurality of blades, each being elongate in cross-section and including a leading edge and a trailing edge, wherein said plurality of blades are positioned transversely across said passageway in staggered relation to each other and said plurality of blades each extend along a respective plane, all of which are parallel to said longitudinal axis.

2. The mouthpiece of claim 1, wherein said leading and trailing edges are sharp.

3. The mouthpiece of claim 2, where the distance between said leading and trailing edges is between 3.8 mm and 4.8 mm.

4. The mouthpiece of claim 1, wherein said blades are arranged in columns.

5. The mouthpiece of claim 4, wherein said blades arranged in any said column are separated by between 1.5 mm and 2.5 mm.

6. The mouthpiece of claim 4, wherein said blades arranged in any said column are separated by between 1.8 mm and 2.2 mm.

7. The mouthpiece of claim 4, where the distance between said leading and trailing edges between 4.1 mm and 4.5 mm.

8. The mouthpiece of claim 4, wherein said blades in any said column are separated from said blades in another said column by between 4 mm and 5 mm.

9. The mouthpiece of claim 4, wherein said blades in any said column are separated from said blades in another said column by 4.5 mm.

10. The mouthpiece of claim 1, wherein said leading and trailing edges lie in a plane that is parallel to said direction of travel of said medicament from said inlet to said outlet.

11. The mouthpiece of claim 1, wherein each said blade has a maximum thickness of between 0.6 mm and 1.2 mm.

12. The mouthpiece of claim 1, wherein each said blade has a maximum thickness of 0.9 mm.

13. The mouthpiece of claim 1, further comprising particle deflectors in said passageway.

14. The mouthpiece of claim 1, wherein said blades are positioned substantially parallel to each other.

15. A method of breaking up particulate in a medicament inhaler, comprising the steps of:
    (a) providing a mouthpiece comprising:
        a passageway extending along a longitudinal axis and having an inlet and an outlet for said particulate to be drawn through; and
        a plurality of blades, each being elongate in cross-section and including a leading edge and a trailing edge, wherein said plurality of blades are positioned transversely across said passageway in staggered relation to each other and said plurality of blades each extend along a respective plane, all of which are parallel to said longitudinal axis; and
    (b) drawing said particulate through said passageway so that said particulate collides with said blades.

* * * * *